(12) United States Patent
Song

(10) Patent No.: US 11,596,387 B2
(45) Date of Patent: Mar. 7, 2023

(54) INTRALUMINAL ULTRASOUND IMAGING DEVICE AND METHOD OF FABRICATING THE SAME

(71) Applicant: KONINKLIJKE PHILIPS N.V., Eindhoven (NL)

(72) Inventor: Jun Song, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 393 days.

(21) Appl. No.: 16/758,944

(22) PCT Filed: Oct. 31, 2018

(86) PCT No.: PCT/EP2018/079776
§ 371 (c)(1),
(2) Date: Apr. 24, 2020

(87) PCT Pub. No.: WO2019/086496
PCT Pub. Date: May 9, 2019

(65) Prior Publication Data
US 2021/0177377 A1 Jun. 17, 2021

Related U.S. Application Data

(60) Provisional application No. 62/579,204, filed on Oct. 31, 2017.

(51) Int. Cl.
*H05K 1/18* (2006.01)
*A61B 8/00* (2006.01)
(Continued)

(52) U.S. Cl.
CPC ............ *A61B 8/445* (2013.01); *A61B 8/0891* (2013.01); *A61B 8/12* (2013.01); *H05K 1/189* (2013.01);
(Continued)

(58) Field of Classification Search
CPC .. H05K 1/18; H05K 1/187–189; H05K 3/305; H05K 3/388; H05K 3/3421;
(Continued)

(56) References Cited

U.S. PATENT DOCUMENTS 6,641,540 B2  11/2003  Fleischman
6,776,763 B2   8/2004  Nix
(Continued)

FOREIGN PATENT DOCUMENTS

WO  2008001282 A2  1/2008
WO  2017168290 A1  10/2017

OTHER PUBLICATIONS

International Search Report & Written Opinion, for PCT/EP2018/079776, dated Feb. 13, 2019.

*Primary Examiner* — Tuan T Dinh

(57) ABSTRACT

Intraluminal ultrasound imaging device, systems and methods (e.g., method of fabricating the device) are provided. In some embodiments, the intraluminal ultrasound imaging device includes a flexible elongate member configured to be positioned within a body lumen of a patient, and an ultrasound scanner assembly disposed at a distal portion of the flexible elongate member and configured to obtain imaging data of the body lumen. The ultrasound scanner assembly includes a flexible substrate, a first under-bump metallization (UBM) layer over the flexible substrate, a first solder feature over the first UBM layer, and a first electronic component electrically connected to the first solder feature.

18 Claims, 11 Drawing Sheets

(51) Int. Cl.
*A61B 8/08* (2006.01)
*A61B 8/12* (2006.01)
*H05K 3/30* (2006.01)
*H05K 3/34* (2006.01)

(52) U.S. Cl.
CPC ........... *H05K 3/305* (2013.01); *H05K 3/3421* (2013.01); *H05K 2201/056* (2013.01); *H05K 2201/10151* (2013.01)

(58) Field of Classification Search
CPC ... H05K 2201/056; H05K 2201/10151; H05K 2201/10145; H05K 2201/10154; A61B 8/445; A61B 8/0891; A61B 8/12; A61B 8/4461; A61B 8/4483
USPC ......... 600/437–467; 361/760–764, 772–774, 361/782–784
See application file for complete search history.

(56) References Cited

U.S. PATENT DOCUMENTS

| | | | |
|---|---|---|---|
| 7,226,417 | B1 | 6/2007 | Eberle |
| 7,846,101 | B2 | 12/2010 | Eberle |
| 10,293,374 | B2 * | 5/2019 | Torashima ......... G01N 29/2418 |
| 2004/0121267 | A1 | 6/2004 | Jang |
| 2007/0205520 | A1 * | 9/2007 | Chou ..................... H01L 24/12 |
| | | | 257/E23.129 |
| 2008/0164543 | A1 | 7/2008 | Ziglioli |
| 2008/0259725 | A1 * | 10/2008 | Bayram ................ B06B 1/0292 |
| | | | 367/181 |
| 2011/0071397 | A1 | 3/2011 | Wodnicki |
| 2013/0257224 | A1 | 10/2013 | Wodnicki |
| 2015/0305710 | A1 | 10/2015 | Stigall |
| 2016/0029999 | A1 * | 2/2016 | Corl ..................... A61B 8/4494 |
| | | | 600/463 |
| 2017/0136496 | A1 * | 5/2017 | Jacobs .................. B06B 1/0292 |

* cited by examiner

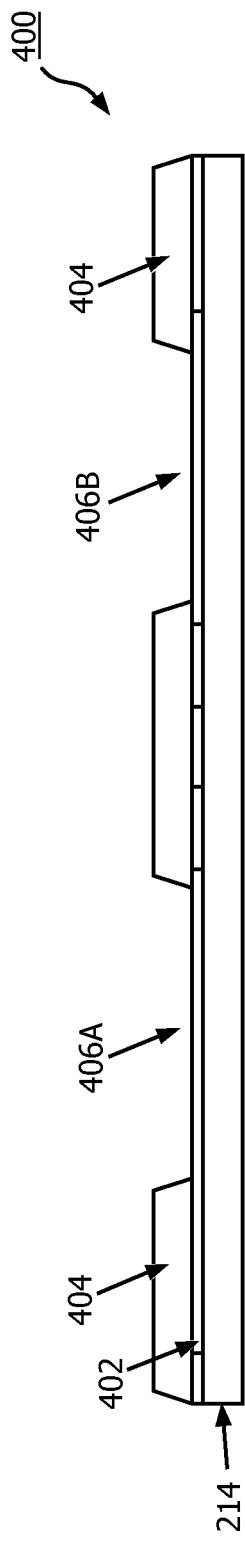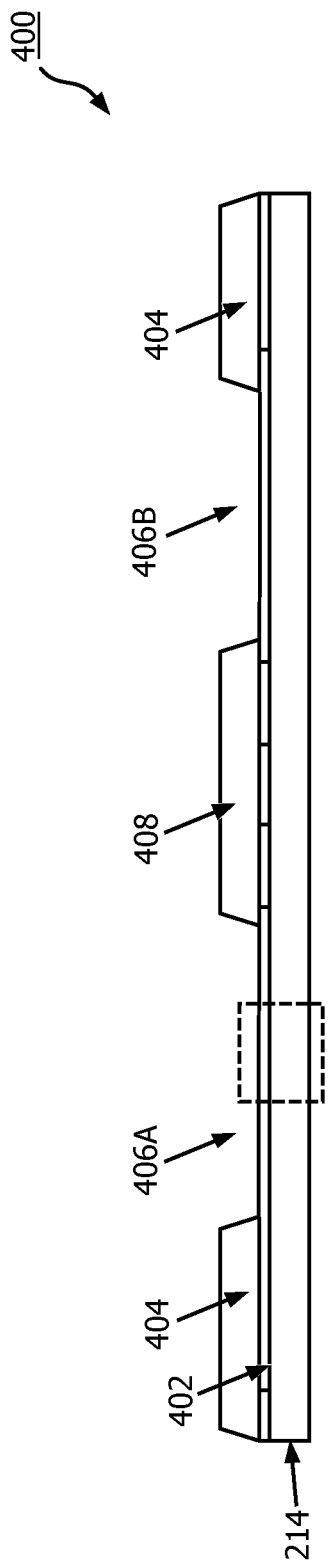

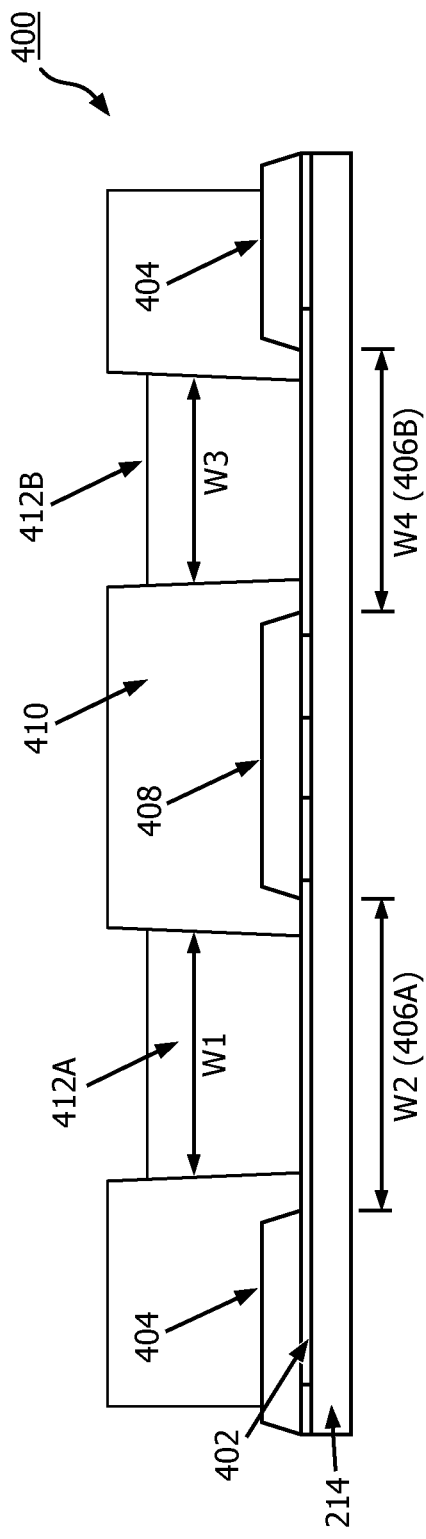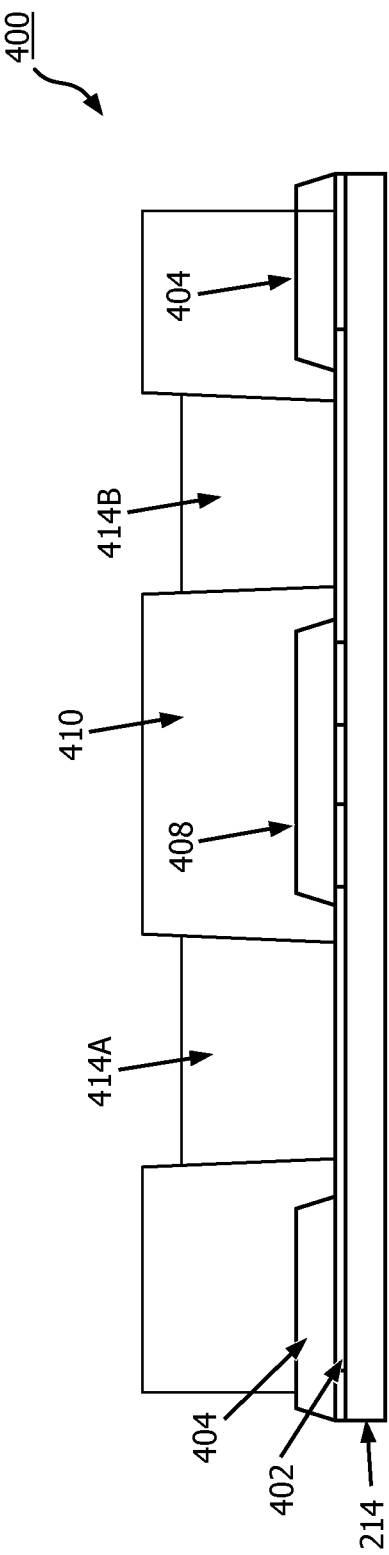

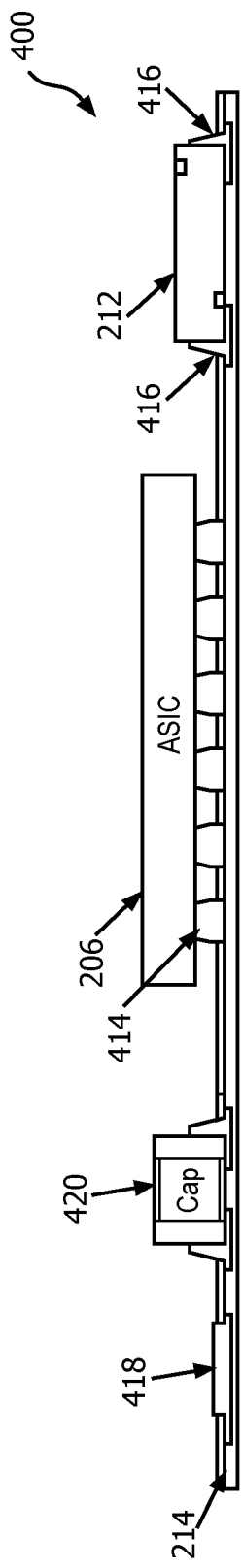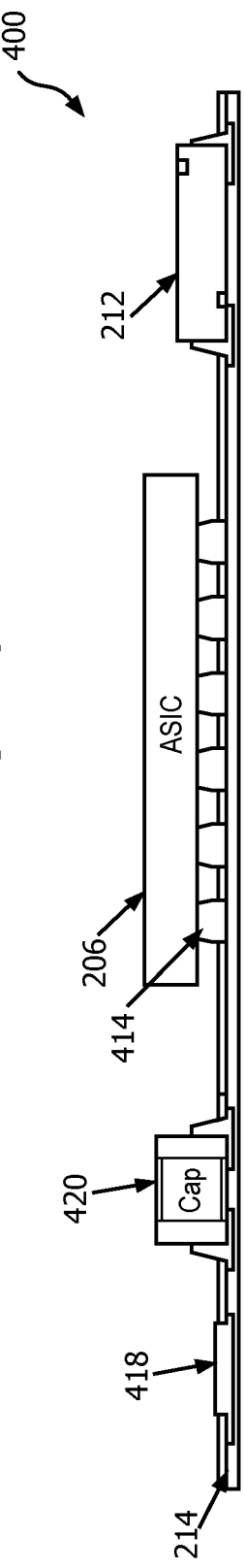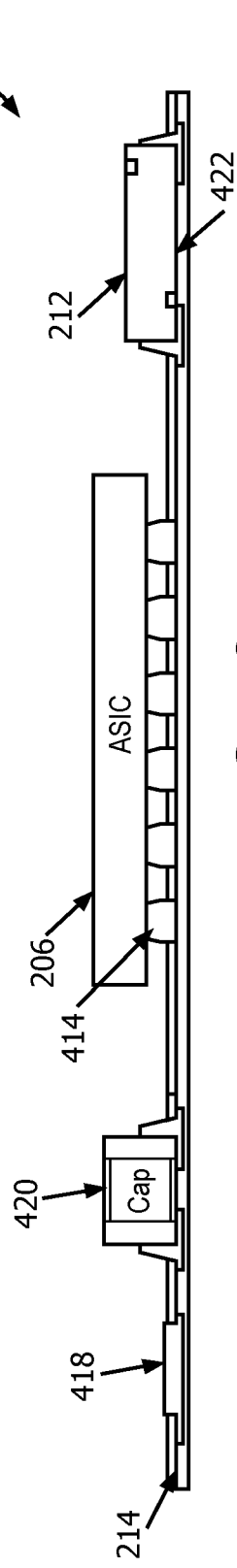

INTRALUMINAL ULTRASOUND IMAGING DEVICE AND METHOD OF FABRICATING THE SAME

RELATED APPLICATION

This application claims the benefit of and priority to U.S. Provisional No. 62/579,204, filed Oct. 31, 2018, which is incorporated by reference herein.

TECHNICAL FIELD

The present disclosure relates generally to intraluminal and/or intravascular ultrasound (IVUS) imaging systems and, in particular, to ultrasound scanner assemblies with electroplated solder bumps. The electroplated solder bumps reduce or eliminate use of solder balls, and increase process yield and reliability of ultrasound scanner assemblies.

BACKGROUND

Minimally invasive sensing systems are routinely utilized by medical professionals to evaluate, measure, and diagnose conditions within the human body. As one example, intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device includes one or more ultrasound transducers arranged at a distal end of an elongate member. The elongate member is passed into the vessel thereby guiding the transducers to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

One type of IVUS devices in use today is a solid-state IVUS device. A typical solid-state IVUS device includes a flexible elongate member, such as a catheter, and an ultrasound scanner assembly positioned on a distal portion of the flexible elongate member. The ultrasound scanner assembly would include an array of ultrasound transducers mounted on a flexible circuit. The array of ultrasound transducers are connected to a set of controllers also mounted on the flexible circuit. The controllers select one or more ultrasound transducers of the array for transmitting an ultrasound pulse and for receiving the echo signal. By stepping through a sequence of transmit-receive sets, a console coupled to the solid-state NUS device can synthesize the effect of a mechanically scanned transducer element but without moving parts.

Conventionally, solder balls and stencil printing are used to bond ultrasound transducers, controllers and other electronic components to the flexible circuit. However, as the sizes of the solder joints for mounting electronic components to the flexible circuit are small, void or unreliable connections are observed at the solder joints. In addition, stencil printing requires precise control of alignment and has a limited range in terms of the amount of solder paste that can be printed onto contact pads of the flexible circuit.

SUMMARY

Embodiments of the present disclosure provide an ultrasound imaging device that includes an ultrasound scanner assembly and methods of fabricating the ultrasound scanner assembly. Electronic components such as ultrasound transducers, capacitors, and application specific integrated circuits (ASICs) are bonded to a flexible circuit without use of solder balls. An under-bump metallization (UBM) layer that includes at least a layer of titanium-tungsten is deposited on the entire surface of the flexible circuit. A dry photoresist layer is then formed over the UBM layer and is patterned with photolithography processes to define bump landing areas. A solder material is electroplated onto the bump landing area to form solder features, using the UBM layer as an electrode. After the patterned dry photoresist layer is removed, the UBM layer not covered by the solder features is removed. Electronic components are then flipped and soldered to the flexible circuit via the solder features. The resultant ultrasound scanner assembly includes UBM layers between solder features and conductive layer of the flexible circuit. Advantageously, the devices, systems, and methods described herein provide a reliable and robust process to bond electronic components to a flexible circuit when fabricating an ultrasound scanner assembly for an NUS device.

In one embodiment, an intraluminal ultrasound imaging device is provided. The intraluminal ultrasound imaging device includes a flexible elongate member configured to be positioned within a body lumen of a patient, and an ultrasound scanner assembly disposed at a distal portion of the flexible elongate member and configured to obtain imaging data of the body lumen. The ultrasound scanner assembly includes a flexible substrate, a first under-bump metallization (UBM) layer over the flexible substrate, a first solder feature over the first UBM layer, and a first electronic component electrically connected to the first solder feature. In some embodiments, the ultrasound scanner assembly of the intraluminal ultrasound imaging device further includes a second UBM layer over a second contact area of the flexible substrate; a second solder feature over the second UBM layer; and a second electronic component electrically connected to the second solder feature. In some implementations, the UBM layer of the intraluminal ultrasound imaging device is disposed over a first contact area of the flexible substrate and the second UBM layer is disposed over a second contact area of the flexible substrate. Each of the first and second contact areas includes a gold top layer and at least one of the first and second UBM layers includes a titanium-tungsten bottom layer in direct contact with the gold top layer. In some instances, the first UBM layer has a first width and the first solder feature has a second width greater than the first width, and the second UBM layer has a third width and the second solder feature has a fourth width greater than the third width. In some embodiments, the first electronic component of the intraluminal ultrasound imaging device includes an ultrasound transducer, an application specific integrated circuit (ASIC) or a capacitor. In some implementations, the second electronic component includes an ultrasound transducer, an ASIC or a capacitor. In some instances, the first electronic component is an ultrasound transducer and the first electronic component further includes an underfill material layer between and the first electronic component and the flexible substrate.

In another embodiment, a method for fabricating an intraluminal ultrasound scanner assembly is provided. The method includes providing a flexible circuit structure, wherein the flexible circuit structure includes a flexible circuit, an under-bump metallization (UBM) layer over a contact area of the flexible circuit, and a solder feature over the UBM layer; applying a solder flux over the solder feature; placing an ultrasound transducer over the flexible circuit structure such that a contact pad of the ultrasound transducer is aligned and in contact with the solder feature; and performing a first reflow soldering process to the flexible circuit structure to bond the contact pad and the solder feature. In some embodiments, the method further includes after performing the first reflow soldering process, removing the solder flux from the flexible circuit structure. In some embodiments, removing the solder flux from the flexible circuit structure includes rinsing the flexible circuit structure with deionized water, and baking the flexible circuit structure to remove the deionized water. The method for fabricating an intraluminal ultrasound scanner assembly further includes forming an underfill material layer between the ultrasound transducer and the flexible circuit structure.

In some embodiments, forming the underfill material layer between the ultrasound transducer and the flexible circuit structure includes dispensing an underfill material between the ultrasound transducer and the flexible circuit structure; and curing the underfill material between the ultrasound transducer and the flexible circuit structure. In some embodiments, curing the underfill material includes performing a second reflow soldering process to the flexible circuit structure. In some implementations, providing the flexible circuit structure includes fabricating the flexible circuit structure. Fabricating the flexible circuit includes providing the flexible circuit, depositing an under-bump metallization (UBM) layer over the polymer insulation layer and the plurality of contact areas of the conductive layer, forming a dry photoresist layer over the UBM layer, selectively removing portions of the dry photoresist layer over a plurality of bump landing areas, each of the plurality of bump landing areas positioned within one of the plurality of contact areas, electroplating a solder material over the plurality of bump landing areas; removing residual portions of the dry photoresist layer; and removing portions of the UBM layer outside of the plurality of bump landing areas. In these embodiments, the flexible circuit includes a flexible substrate, a conductive layer over the flexible substrate, and a polymer insulation layer over the conductive layer. The polymer insulation layer is patterned to exposes a plurality of contact areas of the conductive layer. In some implementations, forming the dry photoresist layer over the UBM layer includes attaching a dry photoresist film to the flexible substrate, and pressing the dry photoresist film against the flexible circuit. In some implementations, selectively removing portions of the dry photoresist layer over the plurality of bump landing areas includes exposing the portions of the dry photoresist layer over the plurality of bump landing areas to a light source, and developing the portions of the dry photoresist layer over the plurality of bump landing areas with a developer solution. In some instances, selectively removing the portions of the dry photoresist layer over the plurality of bump landing areas includes exposing portions of the dry photoresist layer other than the portions over the plurality of bump landing areas to a light source, and developing the portions of the dry photoresist layer over the plurality of bump landing areas with a developer solution. In some embodiments, removing portions of the UBM layer outside of the plurality of bump landing areas includes etching the portions of the UBM layer outside of the plurality of the bump landing areas with an acidic solution.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIGS. 5, 6, 8, 9, 10, 11, 12, 13, 14, 15, 16, 17, and 18 are cross-sectional views of a flexible substrate/circuit/circuit structure being fabricated according to the method of FIGS. 4A and 4B, according to various aspects of the present disclosure.

DETAILED DESCRIPTION

Figure 1:
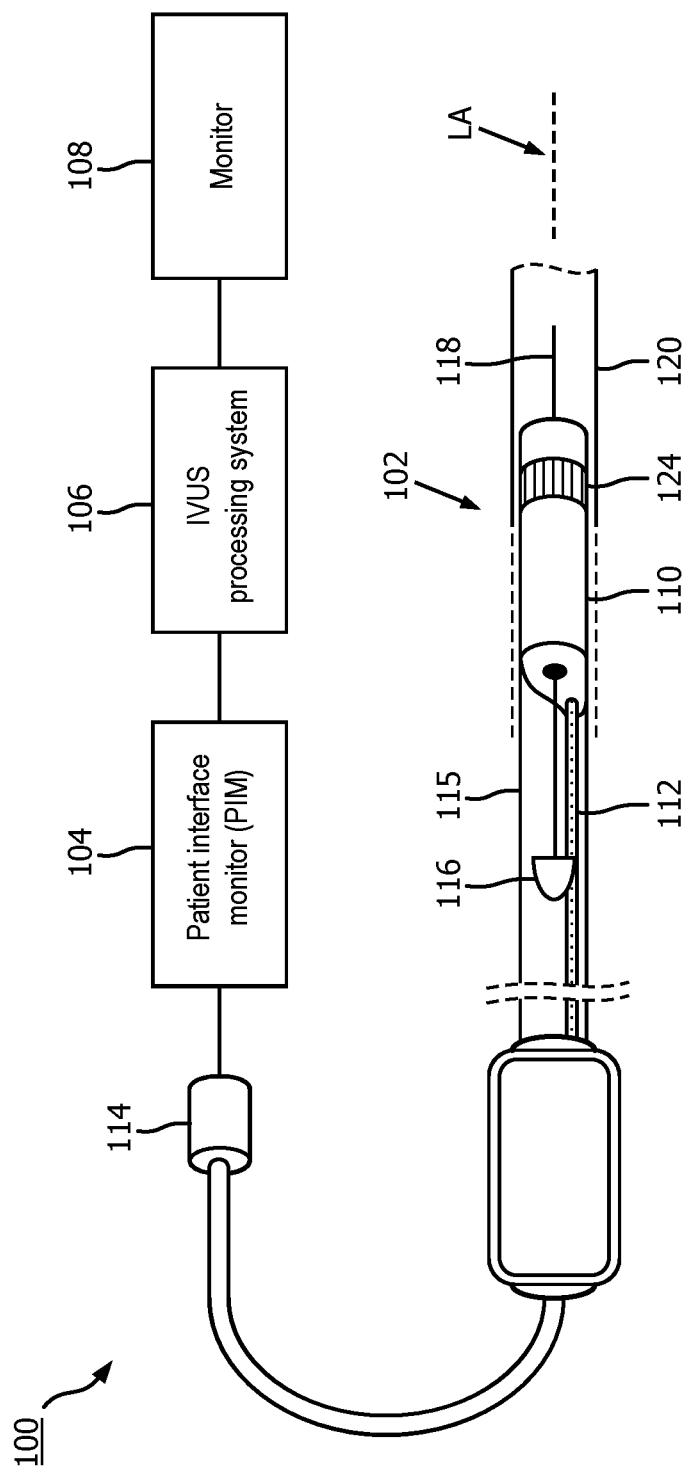
FIG. 1 is a diagrammatic schematic view of an ultrasound imaging system, according to aspects of the present disclosure.

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one or more implementations may be combined with the features, components, and/or steps described with respect to other implementations of the present disclosure. For simplicity, in some instances the same reference numbers are used throughout the drawings to refer to the same or like parts.

FIG. 1 is a diagrammatic schematic view of an intravascular ultrasound (IVUS) imaging system 100, according to aspects of the present disclosure. The IVUS imaging system 100 may include a solid-state IVUS device 102 such as a catheter, guide wire, or guide catheter, a patient interface module (PIM) 104, an IVUS processing system or console 106, and a monitor 108.

At a high level, the IVUS device 102 emits ultrasonic energy from a transducer array 124 included in ultrasound scanner assembly 110 mounted near a distal end of the catheter device. The ultrasonic energy is reflected by tissue structures in the medium, such as a vessel or body lumen 120, surrounding the ultrasound scanner assembly 110, and the ultrasound echo signals are received by the transducer array 124. The PIM 104 transfers the received echo signals (sometimes referred to as imaging data) to the processing system 106 where the ultrasound image (including the flow information) is reconstructed and displayed on the monitor 108. The processing system 106 can include a processor and a memory. The processing system 106 can be operable to facilitate the features of the IVUS imaging system 100 described herein. For example, the processor can execute computer readable instructions stored on the non-transitory tangible computer readable medium.

The PIM 104 facilitates communication of signals between the processing system 106 and the ultrasound scanner assembly 110 included in the IVUS device 102. This communication includes the steps of: (1) providing commands to control logic die(s) 206A, 206B, illustrated in FIG. 2, included in the ultrasound scanner assembly 110 to select the particular transducer array element(s) to be used for transmit and receive, (2) providing the transmit trigger signals to the control logic die(s) 206A, 206B included in the ultrasound scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) of the ultrasound scanner assembly 110. In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage DC power to support operation of the IVUS device 102 including circuitry within the ultrasound scanner assembly 110.

The processing system 106 receives the echo data from the scanner assembly 110 by way of the PIM 104 and processes the data to reconstruct an image of the tissue structures in the medium surrounding the scanner assembly 110. For the example, the IVUS device 102 can be sized and shaped, structurally arranged, and/or otherwise configured to be positioned with a body lumen 120 of the patient. For example, the body lumen 120 can be a vessel in some embodiments. The processing system 106 outputs image data such that an image of the body lumen 120, such as a cross-sectional image of the body lumen (vessel) 120, is displayed on the monitor 108. The body lumen 120 may represent fluid filled or surrounded structures, both natural and man-made. The IVUS device 102 can be referenced as intraluminal imaging device or an intraluminal ultrasound imaging device in some instances. The body lumen 120 may be within a body of a patient. The body lumen 120 may be a blood vessel, such as an artery or a vein of a patient's vascular system, including cardiac vasculature, peripheral vasculature, neural vasculature, renal vasculature, and/or or any other suitable lumen inside the body. For example, the IVUS device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the IVUS device 102 may be used to examine man-made structures such as, but without limitation, heart valves, stents, shunts, filters and other devices.

Figure 2:
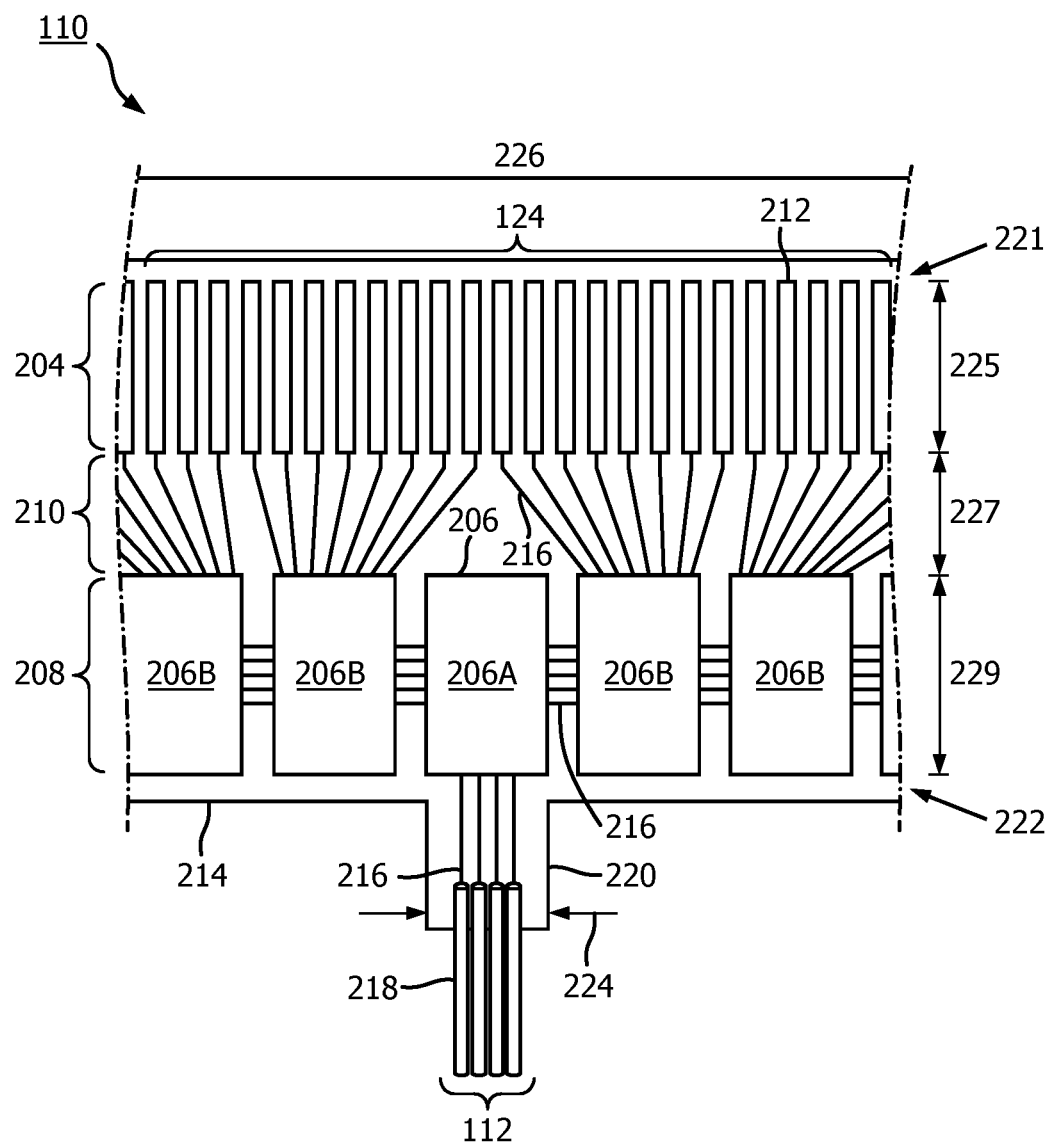
FIG. 2 is a diagrammatic top view of an ultrasound scanner assembly in a flat configuration, according to aspects of the present disclosure.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the ultrasound scanner assembly 110 near a distal end of the IVUS device 102 and an electrical cable 112 extending along the longitudinal body of the IVUS device 102. The electrical cable 112 can include a plurality of conductors, including one, two, three, four, five, six, seven, or more conductors 218 (FIG. 2). It is understood that any suitable gauge wire can be used for the conductors 218. In an embodiment, the electrical cable 112 can include a four-conductor transmission line arrangement with, e.g., 41 AWG gauge wires. In an embodiment, the electrical cable 112 can include a seven-conductor transmission line arrangement utilizing, e.g., 44 AWG gauge wires. In some embodiments, 43 AWG gauge wires can be used.

The electrical cable 112 terminates in a PIM connector 114 at a proximal end of the IVUS device 102. The PIM connector 114 electrically couples the electrical cable 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the body lumen 120.

The IVUS device 102 includes a flexible elongate member 115 having a proximal portion and a distal portion. The ultrasound scanner assembly 110 is positioned at a distal portion of the flexible elongate member 115. The flexible elongate member 115 includes a longitudinal axis LA. The longitudinal axis LA may be associated with the IVUS device 102 and/or the ultrasound scanner assembly 110.

Figure 3:
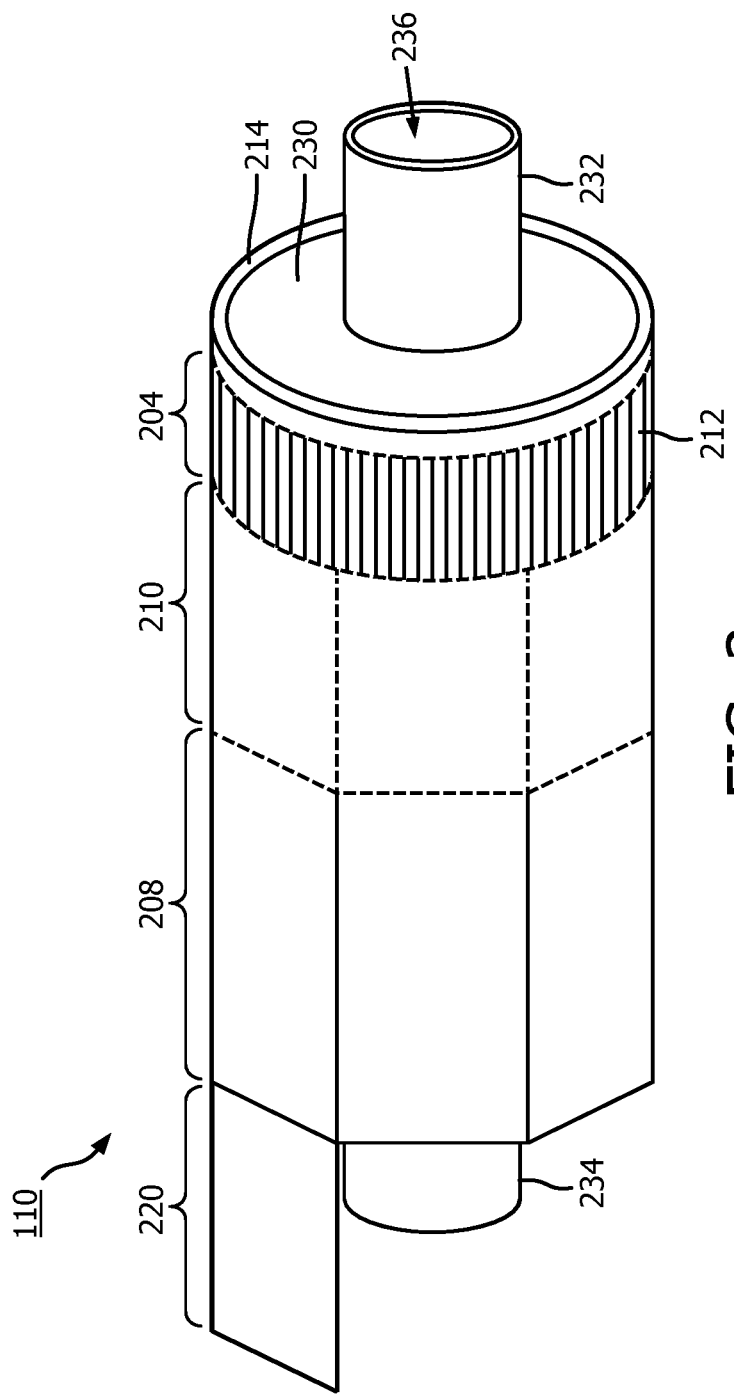
FIG. 3 is a diagrammatic side view of an ultrasound scanner assembly in a rolled configuration around a tubular member, according to aspects of the present disclosure.

FIG. 2 is a top view of a portion of an ultrasound scanner assembly 110 according to an embodiment of the present disclosure. The ultrasound scanner assembly 110 includes a transducer array 124 formed in a transducer region 204 and control logic dies 206 (including control logic dies 206A and 206B) formed in a control region 208, with a transition region 210 disposed therebetween. The control logic dies 206 and the transducers 212 are mounted on a flexible substrate (sometimes referred to as a flexible circuit) 214 that is shown in a flat configuration in FIG. 2. FIG. 3 illustrates a rolled configuration of the flexible substrate 214. The transducer array is a non-limiting example of a medical sensor element and/or a medical sensor element array. The control logic dies 206 is a non-limiting example of a control circuit. The transducer region 204 is disposed adjacent a distal portion 221 of the flexible substrate 214. The control region 208 is disposed adjacent the proximal portion 222 of the flexible substrate 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or a length 227 of the transition region 210 can be greater than lengths 225, 229 of the transducer region and controller region, respectively.

The transducer array 124 may include any number and type of ultrasound transducers 212, although for clarity only a limited number of ultrasound transducers are illustrated in FIG. 2. In an embodiment, the transducer array 124 includes 64 individual ultrasound transducers 212. In a further embodiment, the transducer array 124 includes 32 ultrasound transducers 212. Other numbers are both contemplated and provided for. With respect to the types of transducers, in an embodiment, the ultrasound transducers 212 are piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array includes piezoelectric zirconate transducers (PZT) transducers such as bulk PZT transducers, capacitive micromachined ultrasound transducers (cMUTs), single crystal piezoelectric materials, other suitable ultrasound transmitters and receivers, and/or combinations thereof.

The ultrasound scanner assembly 110 may include various control logic, which in the illustrated embodiment is divided into discrete control logic dies 206. In various examples, the control logic of the ultrasound scanner assembly 110 performs: decoding control signals sent by the PIM 104 across the electrical cable 112, driving one or more transducers 212 to emit an ultrasonic signal, selecting one or more transducers 212 to receive a reflected echo of the ultrasonic signal, amplifying a signal representing the received echo, and/or transmitting the signal to the PIM across the electrical cable 112. In the illustrated embodiment, a ultrasound scanner assembly 110 having 64 ultrasound transducers 212 divides the control logic across nine control logic dies 206, of which five are shown in FIG. 2. Designs incorporating other numbers of control logic dies 206 including 8, 9, 16, 17 and more are utilized in other embodiments. In general, the control logic dies 206 are characterized by the number of transducers they are capable of driving, and exemplary control logic dies 206 drive 4, 8, and/or 16 transducers.

The control logic dies are not necessarily homogenous. In some embodiments, a single controller is designated a master control logic die 206A and contains the communication interface for the electrical cable 112. Accordingly, the master control circuit may include control logic that decodes control signals received over the electrical cable 112, transmits control responses over the electrical cable 112, amplifies echo signals, and/or transmits the echo signals over the electrical cable 112. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

The flexible substrate 214, on which the control logic dies 206 and the transducers 212 are mounted, provides structural support and interconnects for electrical coupling. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). In the flat configuration illustrated in FIG. 2, the flexible substrate 214 has a generally rectangular shape. As shown and described herein, the flexible substrate 214 is configured to be wrapped around a tubular member 230 (FIG. 3) to form a cylindrical toroid in some instances. Therefore, the thickness of the film layer of the flexible substrate 214 is generally related to the degree of curvature in the final assembled ultrasound scanner assembly 110. In some embodiments, the film layer is between 5 μm and 100 μm, with some particular embodiments being between 12.7 μm and 25.1 μm.

To electrically interconnect the control logic dies 206 and the transducers 212, in an embodiment, the flexible substrate 214 further includes conductive traces 216 formed on the film layer that carry signals between the control logic dies 206 and the transducers 212. In particular, the conductive traces 216 providing communication between the control logic dies 206 and the transducers 212 extend along the flexible substrate 214 within the transition region 210. In some instances, the conductive traces 216 can also facilitate electrical communication between the master control logic dies (or master controllers) 206A and the slave control logic dies (or slave controllers) 206B. The conductive traces 216 can also provide a set of conductive pads that contact the conductors 218 of the electrical cable 112 when the conductors 218 of the electrical cable 112 are mechanically and electrically coupled to the flexible substrate 214. Suitable materials for the conductive traces 216 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216 are selected to provide proper conductivity and resilience when the flexible substrate 214 is rolled. In that regard, an exemplary range for the thickness of a conductive trace 216 and/or conductive pad is between 10-50 μm. For example, in an embodiment, 20 μm conductive traces 216 are separated by 20 μm of space. The width of a conductive trace 216 on the flexible substrate 214 may be further determined by the width of the conductor 218 to be coupled to the trace/pad.

The flexible substrate 214 can include a connection interface 220 in some embodiments. The connection interface 220 can be a location of the flexible substrate 214 where the conductors 218 of the electrical cable 112 are coupled to the flexible substrate 214. For example, the bare conductors of the electrical cable 112 are electrically coupled to the flexible substrate 214 at the connection interface 220. The connection interface 220 can be a tab extending from the main body of flexible substrate 214. In that regard, the main body of the flexible substrate 214 can refer collectively to the transducer region 204, controller region 208, and the transition region 210. In the illustrated embodiment, the connection interface 220 extends from the proximal portion 222 of the flexible substrate 214. In other embodiments, the connection interface 220 is positioned at other parts of the flexible substrate 214, such as the distal portion 221, or the flexible substrate 214 omits the connection interface 220. A value of a dimension of the tab or connection interface 220, such as a width 224, can be less than the value of a dimension of the main body of the flexible substrate 214, such as a width 226. In some embodiments, the substrate forming the connection interface 220 is made of the same material(s) and/or is similarly flexible as the flexible substrate 214. In other embodiments, the connection interface 220 is made of different materials and/or is comparatively more rigid than the flexible substrate 214. For example, the connection interface 220 can be made of a plastic, thermoplastic, polymer, hard polymer, etc., including polyoxymethylene (e.g., DELRIN®), polyether ether ketone (PEEK), nylon, and/or other suitable materials. As described in greater detail herein, the tubular member 230, the flexible substrate 214, the connection interface 220 and/or the conductor(s) 218 can be variously configured to facilitate efficient manufacturing and operation of the ultrasound scanner assembly 110.

In some instances, the ultrasound scanner assembly 110 is transitioned from a flat configuration (FIG. 2) to a rolled or more cylindrical configuration (FIG. 3). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND TRANSDUCER ASSEMBLY HAVING A FLEXIBLE SUBSTRATE," each of which is hereby incorporated by reference in its entirety.

As shown in FIG. 3, the flexible substrate 214 is positioned around the tubular member 230 in the rolled configuration. FIG. 3 is a diagrammatic side view with the flexible substrate 214 in the rolled configuration around the tubular member 230, according to aspects of the present disclosure. The tubular member 230 can be referenced as a unibody in some instances. The tubular member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The tubular member 230 can have a distal section 232, a proximal section 234, and a lumen 236 extending longitudinally therethrough. The lumen 236 can be in communication with the exit port 116 and is sized and shaped to receive the guide wire 118 (FIG. 1). The tubular member 230 can be manufactured accordingly to any suitable process. For example, the tubular member 230 can be machined, such as by removing material from a blank to shape the tubular member 230, or molded, such as by an injection molding process. In some embodiments, the tubular member 230 may be integrally formed as a unitary structure, while in other embodiments the tubular member 230 may be formed of different components.

Figure 4A:
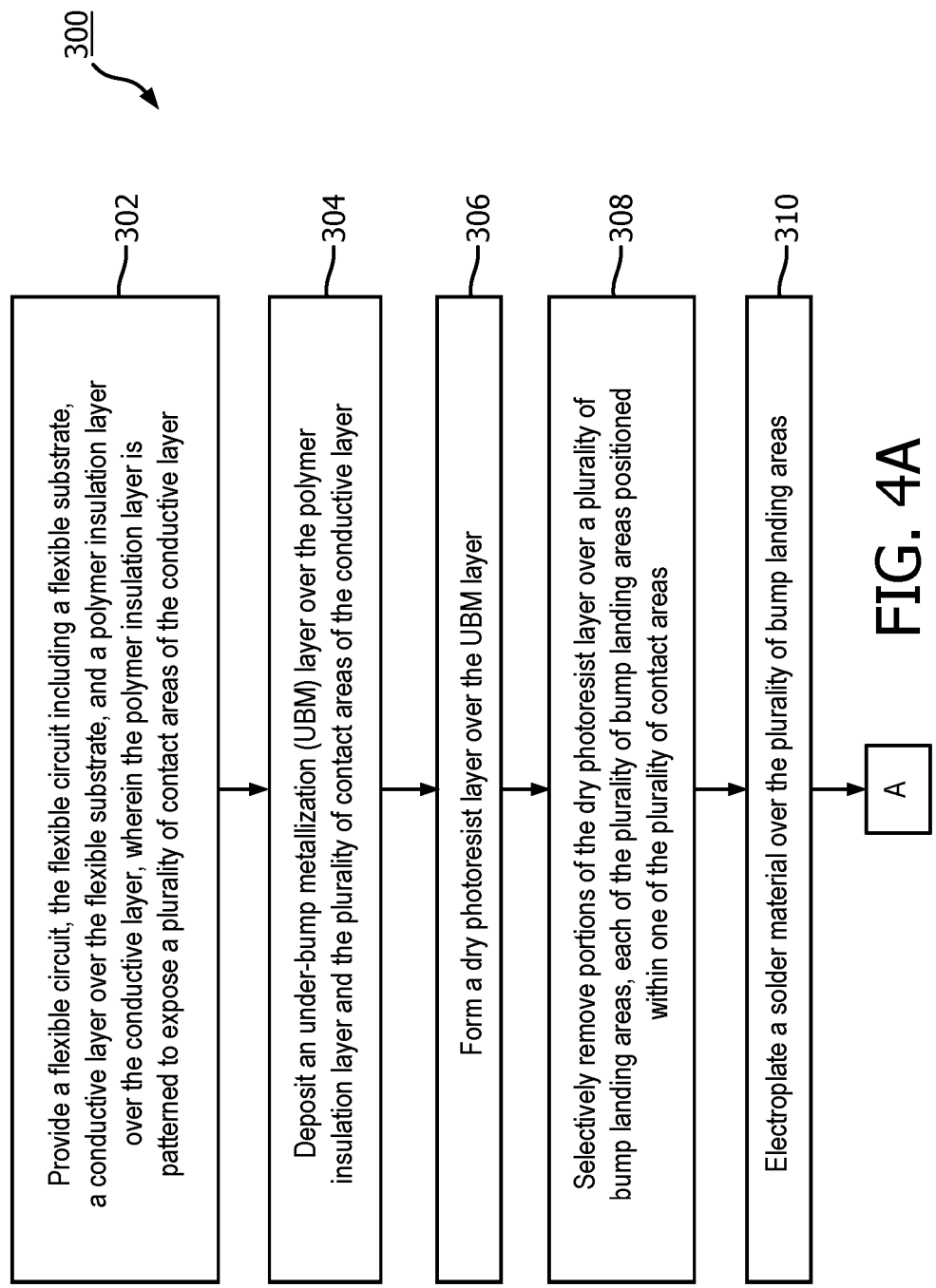
FIGS. 4A and 4B are flow diagram of a method for fabricating an intraluminal ultrasound scanner assembly, according to aspects of the present disclosure.
Figure 4B:
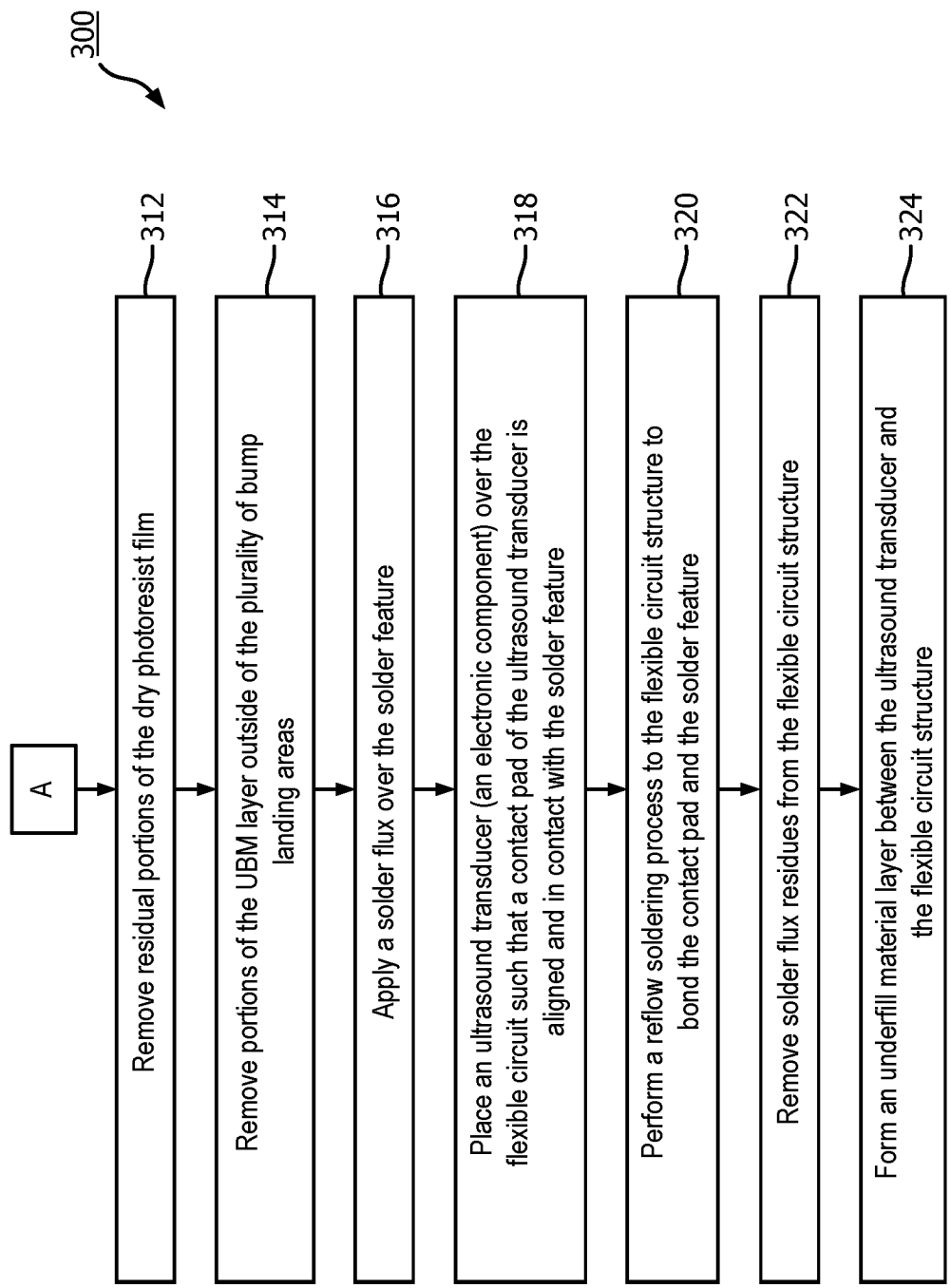

Focus is now turned to the fabrication of the ultrasound scanner assembly 110. Referring to FIGS. 4A and 4B, shown therein is a method 300 for fabricating the ultrasound scanner assembly 110. As shown in FIG. 4A, at operation 302 of method 300, a flexible circuit, such as the flexible circuit 400, shown in FIG. 5, is provided. The flexible circuit 400 includes a flexible substrate 214, a conductive layer 402 over the flexible substrate 214, and a polymer insulation layer 404 over the conductive layer 402. The polymer insulation layer 404 is patterned to expose a plurality of contact areas, such as contact areas 406A and 406B, of the conductive layer 402. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). The polymer insulation layer 404 can be formed of similar materials, such as polyimide, KAPTON™, polyester, polyethylene nathalate, Upilex®, TEFLON®, or polyetherimide.

Reference is now made to FIG. 6. At operation 304 (FIG. 4A) of the method 300, an under-bump metallization (UBM) layer 408 is deposited all over the flexible circuit 400, including over the polymer insulation layer 404 and the plurality of contact areas of the conductive layer 402, such as the contact areas 406A and 406B. The UBM layer 408 functions as a common electrode during the electroplating operation at operation 310 (FIG. 4A). The conductive layer 402 of the flexible circuit 400 is patterned into various shapes according to the design of the circuit and these patterned shapes are not all interconnected. With its substantially uniform deposition thickness, the UBM layer 408 uniformly metalizes the entire surface of the flexible circuit 400. The complete metallization of the surface of the flexible circuit 400 ensures strong and uniform electroplating at operation 310 (FIG. 4A). In some embodiments, the UBM layer 408 can be deposited using sputtering deposition, chemical vapor deposition (CVD), physical vapor deposition (PVD), or plasma enhanced chemical vapor deposition (PE-CVD).

Figure 7:
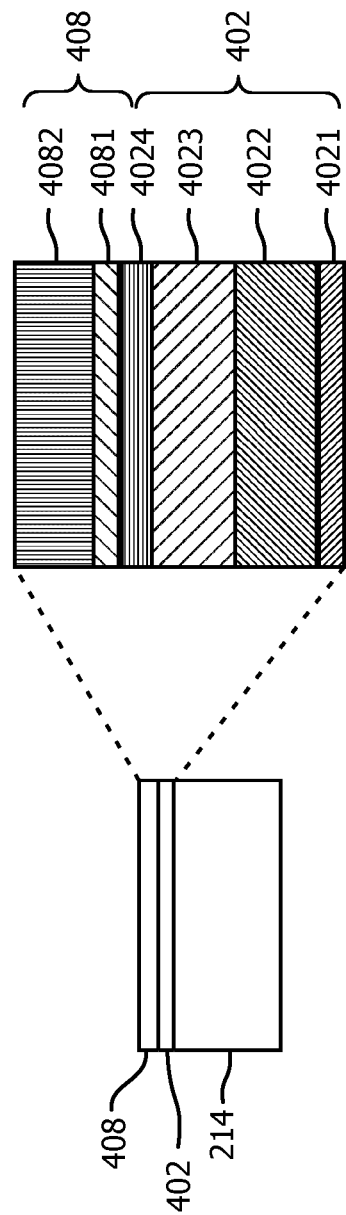
FIG. 7 is a diagrammatic enlarged cross-sectional view of an under-bump metallization (UBM) layer over a conductive layer of a flexible circuit, according to aspects of the present disclosure.

In some embodiments, both the conductive layer 402 and the UBM layer 408 include more than one layer. Referring now to FIG. 7, shown therein is an exemplary embodiment of the layers of the conductive layer 402 and the UBM layer 408. In this embodiment, the conductive layer 402 includes an adhesion layer 4021, a conduction layer 4022, a bather layer 4023, and a protective layer 4024 and the UBM layer 408 includes an adhesion layer 4081 and a conduction layer 4082. In some instances, the adhesion layer 4021 and the adhesion layer 4081 can be formed of titanium-tungsten (Ti—W) pseudo alloy. The adhesion layer 4021 serves at least two functions. First of all, it functions as the interface between the flexible substrate 214 and the rest of the conductive layer 402 and helps the rest of the conductive layer 402 stay attached to the flexible substrate 214. For that reason, the adhesion layer 4021 can also be referred to as an interfacial layer. Second, the adhesion layer 4021 prevents oxygen atoms in the flexible substrate 214 from oxidizing the rest of the conductive layer 402. For that reason, the adhesion layer 4021 can also be referred to as a bather layer. Titanium contributes to the adhesion function due to titanium's mechanical properties while tungsten contributes to the bather function. In instances where the adhesion layer 4021 is formed of Ti—W pseudo alloy, both titanium and tungsten targets are used in a sputtering deposition process. The adhesion layer 4081 of the UBM layer 408 also requires the same properties. The UBM layer 408 is deposited not only on polymer insulation layer 404 but also the plurality of contact areas of the conductive layer 402 (such as contact areas 406A and 406B). As such, the bottom adhesion layer 4081 has to interface with the polymer insulation layer 404 and enhance adhesion to the polymer insulation layer 404. Similarly, the adhesion layer 4081 serves as a barrier layer to prevent oxygen in the polymer insulation layer 404 from oxidizing the conductance layer 4082.

The conduction layer 4082 of the UBM layer 408 and the conduction layer 4022 of the conductive layer 402 are formed of highly conductive metal, such as copper, aluminum or copper-aluminum alloy. The main function of the conduction layers 4082 and 4022 are conduction of electricity. In situations where further processing, such as plating and etching, is to be carried out after formation of the conduction layers, a protective layer advantageously protects the conduction layers from oxidization or being etched away. In the case of the conduction layer 4022, as several more process steps are to be performed, a protective layer 4024 is required to protect damages to and oxidation of the conduction layer 4022. In some embodiments, the protective layer 4024 is formed of gold. Gold is the least reactive metal on earth and can therefore protect the conduction layer 4022 from being oxidized. However, gold can form a solid solution with commonly seen conduction layer material, such as copper. Once the gold protective layer is converted to a gold-copper solid solution, the gold protective layer can no longer protect the conduction layer. To prevent diffusion of copper into the gold protective layer, usually a bather layer (can also be referred to a diffusion bather layer), such as the bather layer 4023 is formed between the conduction layer 4022 and the protective layer 4024. In some embodiments, the bather layer 4023 can be formed of nickel, molybdenum, titanium, tantalum, and cobalt. In some embodiments, a protective layer, such as the protective layer 4024 is formed as the top layer of the conductive layer 402 to provide etching selectivity over the UBM layer 408, which, in some instances, does not have a protective layer. As shown in FIG. 7, in some implementations, the adhesion layer 4081 of the UBM layer 408 is over and in direct contact with the protective layer 4024 of the conductive layer 402.

Figure 8:
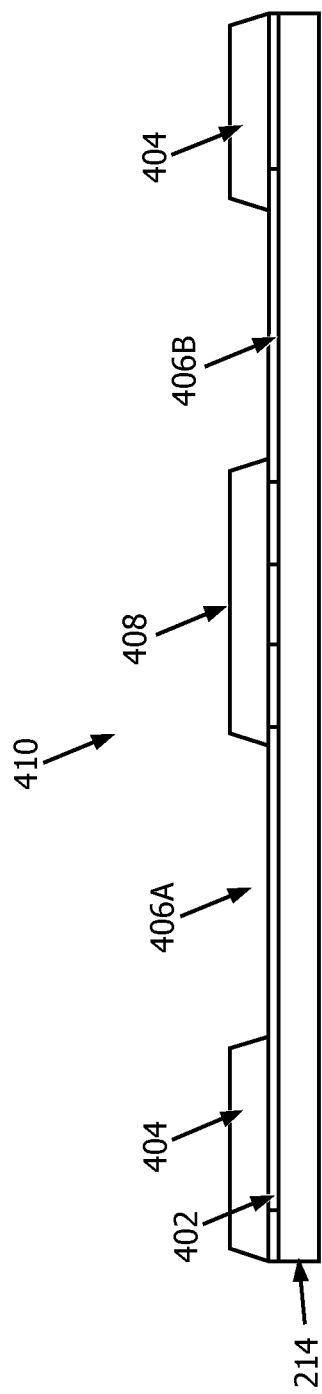

Referring now to FIG. 8, at operation 306 (FIG. 4A) of the method 300, a dry photoresist layer 410 is formed over the UBM layer 408. In some embodiments, the dry photoresist layer 410 is formed by attaching a dry photoresist film to the UBM layer 408 in a roll-to-roll process or a lamination process, where a heated top roller and a heated bottom roller heat press the dry photoresist film onto the UBM layer 408. In these embodiments, the thickness of the dry photoresist layer 410 depends on the thickness of the dry photo resist film used for this operation. The dry photoresist layer 410 can be a positive (or positive tone) or a negative (or negative tone) dry photoresist layer. In embodiments where the dry photoresist layer 410 is a positive dry photoresist layer, when a portion of the dry photoresist layer 410 is exposed to a light source, such as a UV light source, the exposed portion of the dry photoresist layer 410 becomes soluble in a positive developer solution while the rest unexposed portion of the dry photoresist layer 410 is insoluble in the same positive developer solution. If the positive dry photoresist layer 410 is masked with a patterned mask, a positive image of the mask pattern will be transferred to the dry photoresist layer 410 as the portions not masked will be removed during developing. In embodiments where the dry photoresist layer 410 is a negative dry photoresist layer, when a portion of the dry photoresist layer 410 is exposed to a light source, such as a UV light source, the exposed portion of the dry photoresist layer 410 becomes crosslinked/polymerized and therefore insoluble in a negative developer solution that can dissolve the unexposed portion of the dry photoresist layer 410. If the negative dry photoresist layer 410 is masked with a patterned mask, a negative image of the mask pattern will be transferred to the dry photoresist layer 410 as the masked portions will be removed during developing.

Referring now to FIG. 9, at operation 308 (FIG. 4A) of the method 300, portions of the dry photoresist layer 410 over a plurality of bump landing areas, such as bump landing areas 412A and 412B, is selectively removed. Because the bump landing areas 412A and 412B are where the solder bumps (sold features) are to be formed, each of the plurality of the bump landing areas is positioned within one of the plurality of contact areas, such as contact areas 406A and 406B. For illustration purposes, as shown in FIG. 9, the bump landing area 412A is positioned within the contact area 406A and the bump landing area 412B is positioned within the contact area 406B. Along the same line, the width of a bump landing area is smaller than the width of the corresponding contact area. In some embodiments, the widths W1 and W3 of the bump landing areas 412A and the bump landing area 412B are smaller than the width W2 and W4 of the contact areas 406A and 406B, respectively. The operation 308 can be performed using either positive or negative dry photoresist layers. In embodiments where the dry photoresist layer 410 is positive (or positive tone), a mask is laid over the UBM layer 408 such that the would-be bump landing areas, such as bump landing areas 412A and 412B, are exposed. After the masked, positive dry photoresist layer 410 is exposed to a light source, the dry photoresist layer 410 over the would-be bump landing areas becomes soluble in a positive developer solution and can be removed. In embodiments where the dry photoresist layer 410 is negative (or negative tone), a mask is laid over the UBM layer 408 such that the would-be bump landing areas, such as bump landing areas 412A and 412B, are masked. After the masked, negative dry photoresist layer 410 is exposed to a light source, the dry photoresist layer 410 over the would-be bump landing areas remains soluble in a negative developer solution and can be removed. The exposed portions of the negative dry photoresist layer 410 become crosslinked/polymerized and remain on the UBM layer 408.

Reference is now made to FIG. 10. At operation 310 (FIG. 4A) of the method 300, a solder material is electroplated over the plurality of bump landing areas, such as the bump landing areas 412A and 412B, to form solder features 414A and 414B. Because the UBM layer 408 is uniformly deposited over the flexible substrate 214, it serves as an electrode and allows electric current for the electroplating process to go through the entire UBM layer 408. In some embodiments, in the operation 310, the UBM layer 408 serves as the cathode, an anode is made of the solder material to be electroplated, and both the cathode and anode are immersed in an electrolyte. In some instances, the solder material is tin or tin/lead. In those instances, the electrolyte can include an acid, tin chloride, and lead sulfate. In some implementations, additives are added to the electrolytic solution to improve the uniformity of the electroplated layer. Other conditions being equal, the thickness of the solder features 414A and 414B can be determined by the electroplating time. In general, the longer the electroplating continues, the thicker the solder features 414A and 414B would be. To prevent overflow of the solder features 414A and 414B over the dry photoresist layer 410, the time for electroplating the solder features 414A and 414B is controlled such that heights of the solder features of in the bump landing areas are smaller than the height the of the dry photoresist layer 410. For example, in FIG. 4, the solder feature 414A has a top surface that is lower than a top surface of the dry photoresist layer 410.

Figure 11:
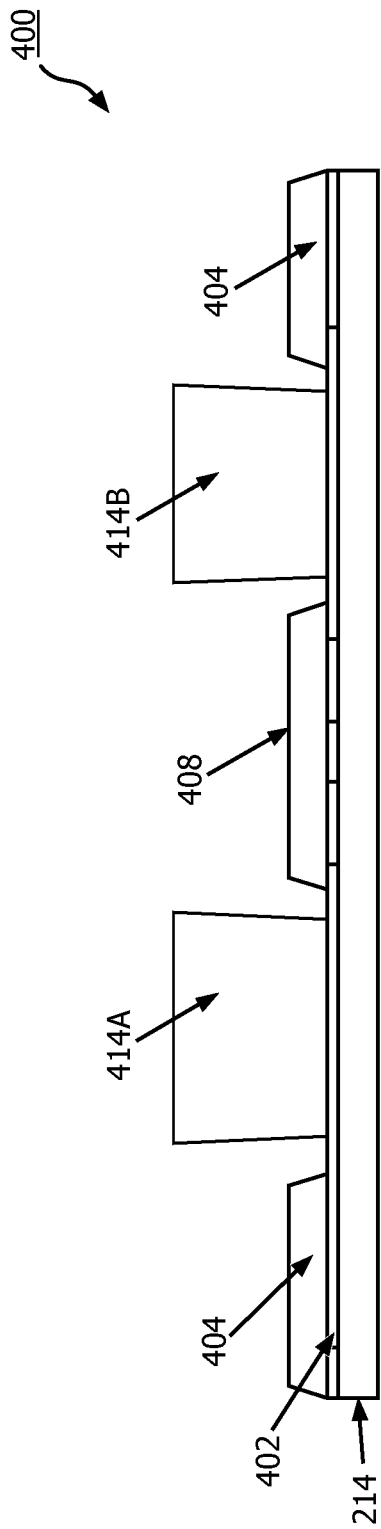

Referring now to FIG. 11, at operation 312 (FIG. 4B) of the method 300, residual portions of the dry photoresist layer 410 are removed from the flexible circuit 400. In some embodiment where a positive dry photoresist film is used to form the dry photoresist layer 410, the residual or leftover dry photoresist layer 410 can be removed by developing the residual dry photoresist layer 410. For example, the residual dry photoresist layer 410 is first exposed to a light source, such as a UV light source. Exposure to the light source makes the residual dry photoresist layer 410 soluble in a positive developer, which is then used to strip away the residual dry photoresist layer 410. In other embodiments where a negative dry photoresist film is used to form the dry photoresist layer 410, an acidic solution can be used to remove the residual dry photoresist layer 410.

Figure 12:
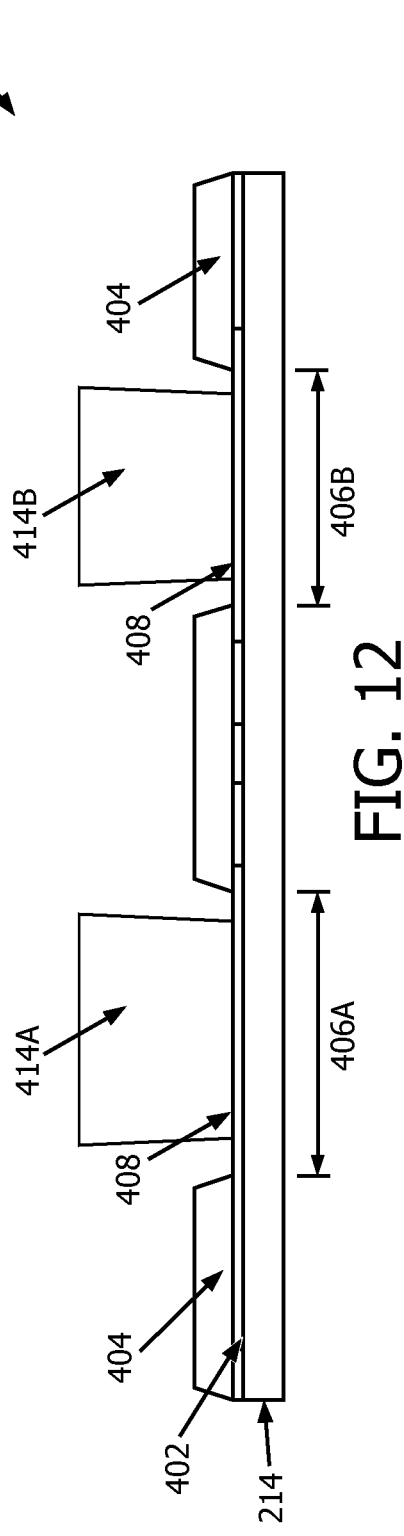

Referring now to FIG. 12, at operation 314 (FIG. 4B) of the method 300, portions of the UBM layer 408 outside of the bump landing areas, such as bump landing areas 412A and 412B, are removed. Because the bump landing areas, such as the bump landing areas 412A and 412B, are now covered by the solder features, such as the solder features 414A and 414B, the operation 314 can also be described as an operation to remove the portions of the UBM layer 408 not cover or protected by the solder features, such as the solder features 414A and 414B. In some embodiments, the removal of the UBM layers 408 not covered by solder features at operation 314 is performed by acid stripping and can be highly selective due to different acid resistance of the materials exposed to the acid. As shown in FIG. 12, if the flexible circuit 400 is subject to acid stripping, the polymer insulation layer 404, the conductive layer 402, the UBM layer 408, and the solder features 414A and 414B are exposed to the acid used in the acid stripping process. Out of them, the polymer insulation layer 404 can be formed of KAPTON™ (trademark of DuPont), which is resistant to many acids; the conductive layer 402 can include a gold top protective layer 4024, which is also acid resistant; and the solder features 414A and 414B can include lead, which is known to exhibit acid resistance. Therefore, the UBM is the least resistant to acid of them all and can be etched away without substantially damaging the polymer insulation layer 404, the conductive layer 402, and the solder features 414A and 414B. Because widths of solder features 414A and 414B are smaller than the corresponding widths of the contact areas 406A and 406B, upon completion of the operation 314, widths of the portions of the UBM layer 408 under the solder features 414A and 414B are going to be smaller than the widths of the corresponding contact areas 406A and 406B.

To differentiate the flexible circuit 400 shown in FIGS. 5 and 6 and the flexible circuit 400 with solder features, such as those shown in FIGS. 12-18, sometimes the flexible circuit 400 without solder features are referred to simply as a flexible circuit and the flexible circuit 400 with solder features are referred to as a flexible circuit structure. However, as these references are essentially made to a flexible circuit throughout a fabrication process, these references are used interchangeably and their differences in features can only be ascertained by the context of the relevant descriptions. In addition, while a flexible substrate is used to refer to the substrate 214 of the flexible circuit 400 in FIGS. 5-18, it can also be used to refer to the flexible circuit or the flexible circuit structure in certain context. This is so because the flexible circuit/flexible circuit structure can be viewed as the substrate for the purposes of mounting the electronic components. In that sense, the flexible circuit/flexible circuit structure is the substrate for the electronic components. People skilled in the art would appreciate the necessary flexibility of these usages and definitions.

Figure 13:
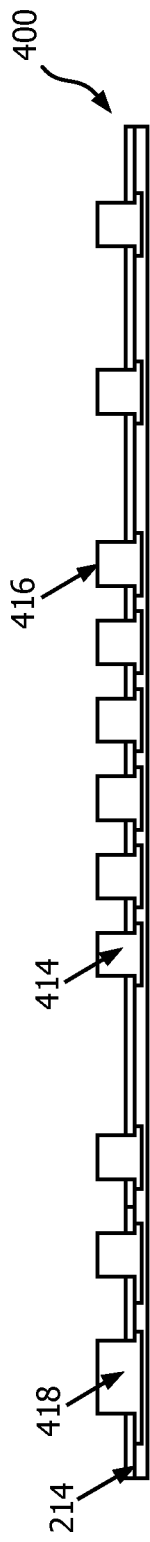

Referring now to FIG. 13, shown therein an expanded view of the flexible circuit 400 that includes multiple solder features in addition to the solder features 414A and 414B. At operation 316 (FIG. 4B) of the method 300, solder flux is applied over the solder features to form a solder flux layer 416. In some embodiments, solder flux is jet-printed onto each of the solder features by a solder flux printer. In some other embodiments, solder flux is printed onto each of the solder features with use of a stencil. In some instances, a stencil is a laser cut stainless steel foil with openings matching the locations and areas of the solder features. Solder flux can serve as a reducing agent during a subsequent soldering process to prevent formation of oxide in the solder and the joining surface. Solder flux can also help remove oxide and facilitate soldering. In some embodiments, the solder flux is water based and is tacky. The tackiness of the solder flux allows electronic components to be temporarily attached to the corresponding solder features before solder joints are formed. What is also shown in FIG. 13 is a wire attachment pad 418. In some embodiments, wire attachment pads, such as the wire attachment pad 418, are positioned at a proximal portion of the flexible circuit 400 and are used to bond to conductive traces 216 shown in FIG. 2.

Figure 14:
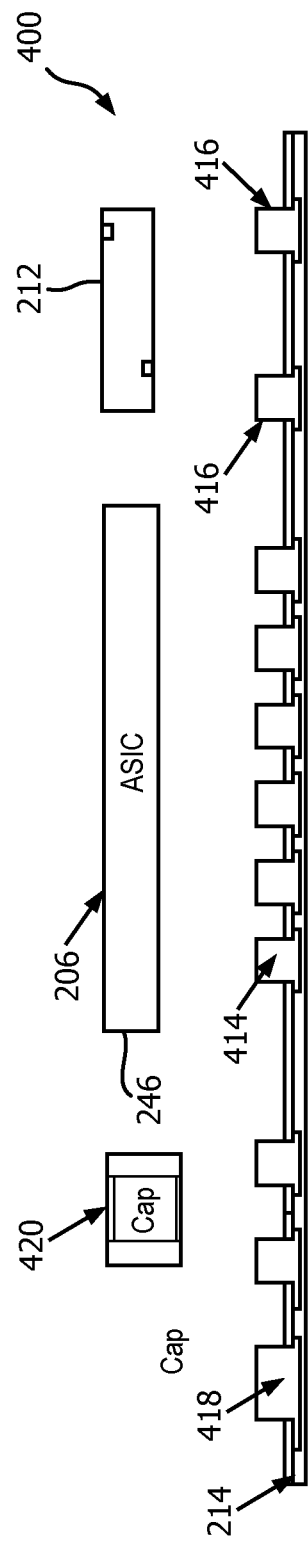
Figure 15:
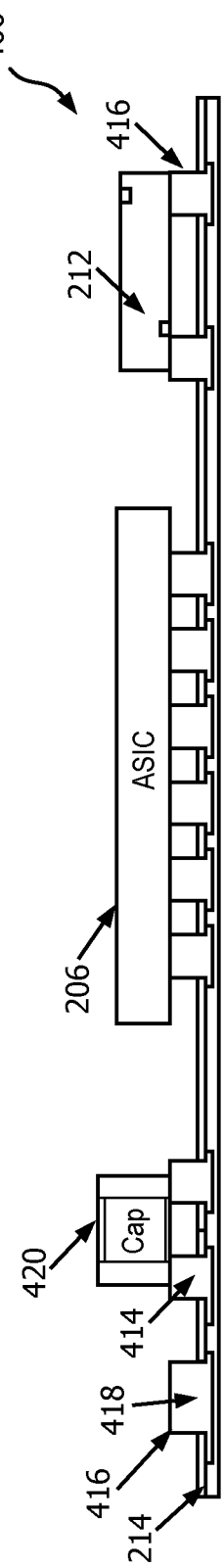

Referring now to FIGS. 14 and 15, at operation 318, various electronic components, including but not limited to a capacitor 420, an application specific integrated circuit (ASIC) or control logic die 206, and a transducer 212, are placed over the flexible circuit structure 400 such that contact pads of the electronic component is aligned and in contact with the solder features. Each of the electronic components has one or more contact pads. For example, the capacitor 420 has two contact pads on either end thereof. The ASIC 206 shown in FIG. 14 has six contact pads 246. Please note that the ASIC 206 can have less or more than 6 contact pads 246, depending on the design and complexity of the ASIC 206. The design that the contact pads of the ASIC 206 face the solder features 414 on the flexible circuit structure 400 is sometimes referred to as flip chip or flip chip design. The flip chip design allows bonding of the ASIC 206 to the flexible circuit structure 400 without any wires. Thanks to the tackiness of the solder flux layer 416, once the capacitor 420, the ASIC 206, and the transducer 212 is put in contact with the solder features 414, they are temporarily held in place by the solder flux during transport of the flexible circuit structure 400 to a subsequent processing station for further processing. Solder can electrically and/or mechanically attach, connect and/or otherwise couple one or more electronic components to the flexible substrate and/or one or more other electronic components on the flexible substrate.

As shown in FIG. 16, at operation 320, a reflow soldering process is performed to the flexible circuit structure 400 to solder or bond the contact pads and corresponding solder features 414. In some embodiments, the reflow soldering process is performed by placing the flexible circuit structure 400 in a reflow oven. This operation can sometimes be referred to as the reflow process or a reflow soldering process. During the reflow process, the solder features can become flowable and gradually wet and fill the entire contact areas. Because the width and area of the contact areas are greater and larger than the corresponding bump landing area, the final height of the solder feature after the reflow process is going to be smaller than the initial height of the solder feature before the reflow process. For example, the contact area 406A shown in FIG. 9 has the width W2 that is greater than the width W1 of the bump landing area 412A. In general, the area of the contact area and the area of the bump landing area are proportional to the square product of the width. It follows that the area of the contact area 406A is greater than the area of the bump landing area 412A. Reference is now made to FIG. 12. When the solder feature 414A becomes flowable during the reflow soldering process at operation 320, the solder in the solder feature 414A has the tendency to wet the surfaces within the contact area 406A and fill the space defined by the contact area 406A and the surrounding polymer insulation layers 404. Due to the increase in area of the base, the solder feature 414A will decrease in its height. In some embodiments, because the UBM layer 408 is narrower/smaller than the contact area 406A, the reflowed solder feature 414A will completely cover all sides and edges of the UBM layer 408. The same phenomenon can be observed in FIG. 16 as well. When compared to the height of the solder features shown in FIG. 15, all solder features in FIG. 16 decrease in height, with their bases generally congruent to the shape of the contact areas beneath.

As shown in FIG. 16, during the reflow soldering process at the operation 320 (FIG. 4B) of the method 300, solder flux residues can move around and accumulate in features with relatively lower height. The solder flux residues are to be removed from the flexible circuit structure 400 at operation 322 (FIG. 4B), as shown in FIG. 17. In some embodiments where the solder flux is water soluble, deionized water (DI water) can be used to wash away the solder flux residues. In some implementations, to enhance the effectiveness of the washing, one or more kinds of surfactants are added into the DI water. In still some other implementations, the solder flux residues removing at the operation 322 is facilitated by agitation brought about by a circulation bath or an ultrasonic bath. After the solder flux residues are washed away, the flexible circuit structure 400 can be rinsed again with DI water and baked in an oven to drive out the moisture.

Referring to FIG. 18, at operation 324 (FIG. 4B) of the method 300, an underfill material layer 422 is formed between the transducer 212 and the flexible circuit structure 400 (or, more precisely, the flexible substrate 214) to provide structural support of the transducer 212. The underfill material layer 422 can be formed of an epoxy or other adhesive. In some instances, the underfill material layer 422 is formed of heat cure epoxy or thermally curable epoxy. In these instances, after the epoxy is dispensed near the transducer 212 and allowed to fill the space underneath the transducer 212, the flexible circuit structure 400 is placed in an oven to cure the epoxy. In some other instances, the underfill material layer 422 is formed of UV cure epoxy or UV-curable epoxy. In these instances, after the epoxy is dispensed and allowed to fill in the space between the transducer 212 and the flexible substrate 214, UV light is shone on at least a part of the underfill epoxy to cure it.

In some embodiments, the thickness of the underfill material layer 422 impacts the center frequency of the transducer 212. In those embodiments, the present disclosure provides a method to adjust the distance between a mounted transducer 212 and the flexible substrate 214. As described above with references to FIGS. 9 and 16, the bases of the solder features cannot be larger than the contact areas and are more often than not, smaller than the contact areas. During the reflow soldering process, the solder feature becomes flowable and is allowed to wet and fill the contact area. For a given amount of solder in a solder feature, the larger the contact area below, the "flatter" of the resultant solder feature will be after the reflow soldering process. Conversely, for the same amount of solder in a solder feature, if the contact area below is small, the resultant solder feature after the reflow soldering process is going to be taller, elevating the electronic components further away from the flexible substrate 214. Please refer to FIGS. 9 and 10. The amount of the solder that can be filled in the bump landing area 412A is determined by the length (along a direction that goes into FIGS. 9 and 10), the width (as labeled in FIG. 9), and the height of the solder feature 414A (measure from the top surface of the UBM layer 408 to the top surface of the solder feature 414A). If the length and height of the solder feature 414A are fixed, the width of the solder feature 414A determines the amount of solder material in the solder feature 414A. That is, by controlling the width of the solder feature 414A, the amount of solder material in the solder feature 414A can be controlled. The thickness of the underfill material layer 422 can therefore be adjusted by adjusting the width of the solder feature 414A and the width of the contact area 406A. For example, when the width of the solder feature 414A is small and the width of the contact area 406A is large, a small amount of solder material is going to be spread out along a larger contact area 406A, resulting in a reduced height of the final solder feature after the reflow soldering process. Whereas, when the width of the solder feature 414A is large and the width of the contact area 406A is small, a large amount of solder material is going to be spread out along a smaller contact area 406A, resulting in an increased height of the final solder feature after the reflow soldering process.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal ultrasound imaging device, comprising:
    a flexible elongate member configured to be positioned within a body lumen of a patient; and
    an ultrasound scanner assembly disposed at a distal portion of the flexible elongate member and configured to obtain imaging data of the body lumen, the ultrasound scanner assembly comprising:
        a flexible substrate,
        a conductive layer over the flexible substrate,
        a first polymer insulation portion and a second polymer insulation portion over the conductive layer, wherein a space between the first polymer insulation portion and the second polymer insulation portion exposes a first contact area of the conductive layer,
        a first under-bump metallization (UBM) layer over the first contact area,
        a first solder feature over the first UBM layer, wherein the first UBM layer and the first solder feature are disposed between the first polymer insulation and the second polymer insulation portion, and
        a first electronic component electrically connected to the first solder feature.

2. The intraluminal ultrasound imaging device of claim 1, wherein the ultrasound scanner assembly further comprising:
    a second UBM layer over a second contact area of the conductive layer;
    a second solder feature over the second UBM layer; and
    a second electronic component electrically connected to the second solder feature.

3. The intraluminal ultrasound imaging device of claim 2, wherein each of the first and second contact areas comprises a gold top layer and at least one of the first UBM layer or the second UBM layer comprises a titanium-tungsten bottom layer in direct contact with the gold top layer.

4. The intraluminal ultrasound imaging device of claim 2, where the first contact area has a first width and the first solder feature has a second width greater than the first width; and
    where the second contact area has a third width and the second solder feature has a fourth width greater than the third width.

5. The intraluminal ultrasound imaging device of claim 2, wherein the second electronic component comprises an ultrasound transducer, an application specific integrated circuit (ASIC) or a capacitor.

6. The intraluminal ultrasound imaging device of claim 1, wherein the first electronic component comprises an ultrasound transducer, an application specific integrated circuit (ASIC) or a capacitor.

7. The intraluminal ultrasound imaging device of claim 1,
wherein the first electronic component is an ultrasound transducer,
wherein the ultrasound scanner assembly further comprises an underfill material layer between the first electronic component and the flexible substrate.

8. A method for fabricating an intraluminal ultrasound scanner assembly, comprising:
providing a flexible circuit structure, the flexible circuit structure comprising:
a flexible substrate,
a conductive layer over the flexible substrate,
a first polymer insulation portion and a second polymer insulation portion over the conductive layer, wherein a space between the first polymer insulation portion and the second polymer insulation portion exposes a contact area of the conductive layer,
an under-bump metallization (UBM) layer over the contact area, and
a solder feature over the UBM layer, wherein the UBM layer and the solder feature are disposed between the first polymer insulation and the second polymer insulation portion;
applying a solder flux over the solder feature;
placing an ultrasound transducer over the flexible circuit structure such that a contact pad of the ultrasound transducer is aligned and in contact with the solder feature; and
performing a first reflow soldering process to the flexible circuit structure to bond the contact pad and the solder feature.

9. The method of claim 8, further comprising:
after performing the first reflow soldering process, removing the solder flux from the flexible circuit structure.

10. The method of claim 9, wherein removing the solder flux from the flexible circuit structure comprises:
rinsing the flexible circuit structure with deionized water; and
baking the flexible circuit structure to remove the deionized water.

11. The method of claim 8, further comprising:
forming an underfill material layer between the ultrasound transducer and the flexible circuit structure.

12. The method of claim 11, wherein forming the underfill material layer between the ultrasound transducer and the flexible circuit structure comprises:
dispensing an underfill material between the ultrasound transducer and the flexible circuit structure; and
curing the underfill material between the ultrasound transducer and the flexible circuit structure.

13. The method of claim 12, wherein curing the underfill material comprises performing a second reflow soldering process to the flexible circuit structure.

14. The method of claim 8,
wherein providing the flexible circuit structure comprises fabricating the flexible circuit structure,
wherein fabricating the flexible circuit structure comprises:
providing the flexible substrate and the conductive layer over the flexible substrate, and
patterning a polymer insulation layer over the conductive layer, thereby exposing a plurality of contact areas of the conductive layer, wherein patterning the polymer insulation portion defines the first polymer insulation portion and the second insulation portion;
depositing the UBM layer over the polymer insulation layer and the plurality of contact areas of the conductive layer;
forming a dry photoresist layer over the UBM layer;
selectively removing portions of the dry photoresist layer over a plurality of bump landing areas, each of the plurality of bump landing areas positioned within one of the plurality of contact areas;
electroplating a solder material over the plurality of bump landing areas, wherein the solder material defines the solder feature;
removing residual portions of the dry photoresist layer; and
removing portions of the UBM layer outside of the plurality of bump landing areas.

15. The method of claim 14, wherein forming the dry photoresist layer over the UBM layer comprises:
attaching a dry photoresist film to the flexible substrate; and
pressing the dry photoresist film against the flexible substrate.

16. The method of claim 14, wherein selectively removing portions of the dry photoresist layer over the plurality of bump landing areas comprises:
exposing the portions of the dry photoresist layer over the plurality of bump landing areas to a light source; and
developing the portions of the dry photoresist layer over the plurality of bump landing areas with a developer solution.

17. The method of claim 14, wherein selectively removing the portions of the dry photoresist layer over the plurality of bump landing areas comprises:
exposing portions of the dry photoresist layer other than the portions over the plurality of bump landing areas to a light source; and
developing the portions of the dry photoresist layer over the plurality of bump landing areas with a developer solution.

18. The method of claim 14, wherein removing portions of the UBM layer outside of the plurality of bump landing areas comprises etching the portions of the UBM layer outside of the plurality of the bump landing areas with an acidic solution.

* * * * *